US00PP18230P2

(12) United States Plant Patent
Kleinhanns

(10) Patent No.: US PP18,230 P2
(45) Date of Patent: Nov. 20, 2007

(54) ***SALVIA* PLANT NAMED 'SENSATION ROSE'**

(50) Latin Name: *Salvia nemorosa*
Varietal Denomination: Sensation Rose

(75) Inventor: Christoph Kleinhanns, Quedlinburg (DE)

(73) Assignee: Rijnbeek en Zoon B.V., Boskoop (NL)

( * ) Notice: Subject to any disclaimer, the term of this patent is extended or adjusted under 35 U.S.C. 154(b) by 98 days.

(21) Appl. No.: 11/323,169

(22) Filed: Dec. 30, 2005

(51) Int. Cl.
*A01H 5/00* (2006.01)

(52) U.S. Cl. ..... Plt./226
(58) Field of Classification Search ..... Plt./226
See application file for complete search history.

*Primary Examiner*—Kent Bell
(74) *Attorney, Agent, or Firm*—C. A. Whealy

(57) ABSTRACT

A new and distinct cultivar of *Salvia* plant named 'Sensation Rose', characterized by its upright, somewhat outwardly spreading and compact plant habit; freely branching habit; freely flowering habit; red purple-colored flowers; and good garden performance.

2 Drawing Sheets

Botanical designation: *Salvia nemorosa.*
Cultivar denomination: 'Sensation Rose'.

BACKGROUND OF THE INVENTION

The present Invention relates to a new and distinct cultivar of *Salvia* plant, botanically known as *Salvia nemorosa,* and hereinafter referred to by the name 'Sensation Rose'.

The new *Salvia* is a product of a planned breeding program conducted by the Inventor in Quedlinburg, Germany. The objective of the breeding program was to create new compact *Salvia* cultivars that flower early.

The new *Salvia* originated from a cross-pollination made by the Inventor in December, 2000 of a proprietary *Salvia nemorosa* selection identified as code number MD1700, not patented, as the female, or seed, parent with a proprietary *Salvia nemorosa* selection identified as code number 60608810, not patented, as the male, or pollen, parent. The new *Salvia* was discovered and selected by the Inventor as a single flowering plant within the progeny of the stated cross-pollination grown in a controlled environment in Quedlinburg, Germany in 2002.

Asexual reproduction of the new cultivar by cuttings at Quedlinburg, Germany, since September, 2002, has shown that the unique features of this new *Salvia* are stable and reproduced true to type in successive generations.

SUMMARY OF THE INVENTION

Plants of the cultivar 'Sensation Rose' have not been observed under all possible environmental conditions. The phenotype may vary somewhat with variations in environment such as temperature and light intensity without, however, any variance in genotype.

The following traits have been repeatedly observed and are determined to be the unique characteristics of 'Sensation Rose'. These characteristics in combination distinguish 'Sensation Rose' as a new and distinct *Salvia* cultivar:

1. Upright, somewhat outwardly spreading and compact plant habit.
2. Freely branching habit.
3. Freely flowering habit.
4. Red purple-colored flowers.
5. Good garden performance.

Plants of the new *Salvia* are more compact than plants of the female parent selection. In addition, plants of the new *Salvia* and the female parent selection differ in flower color as plants of the female parent selection have blue-colored flowers.

Plants of the new *Salvia* differ from plants of the male parent selection in the following characteristics:

1. Plants of the new *Salvia* are not as compact as plants of the male parent selection.
2. Plants of the new *Salvia* are more freely branching than plants of the male parent selection.
3. Inflorescences of plants of the new *Salvia* are denser than inflorescences of plants of the male parent selection.
4. Plants of the new *Salvia* have smaller flowers than plants of the male parent selection.
5. Plants of the new *Salvia* and the male parent selection differ in flower color.

Plants of the new *Salvia* can be compared to plants of the *Salvia* cultivar Rose Queen, not patented. In side-by-side comparisons conducted in Quedlinburg, Germany, plants of the new *Salvia* differed from plants of the cultivar Rose Queen in the following characteristics:

1. Plants of the new *Salvia* were more compact than plants of the cultivar Rose Queen.
2. Plants of the new *Salvia* were more freely branching than plants of the cultivar Rose Queen.
3. Inflorescences of plants of the new *Salvia* were denser than inflorescences of plants of the cultivar Rose Queen.

Plants of the new *Salvia* can be compared to plants of the *Salvia* cultivar Rosenwein, not patented. In side-by-side comparisons conducted in Quedlinburg, Germany, plants of the new *Salvia* differed from plants of the cultivar Rosenwein in the following characteristics:

1. Plants of the new *Salvia* were more compact than plants of the cultivar Rosenwein.
2. Plants of the new *Salvia* were more freely branching than plants of the cultivar Rosenwein.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Salvia*.

The photograph on the first sheet comprises a side perspective view of a typical flowering plant of 'Sensation Rose' grown in a container.

The photograph at the top of the second sheet is a close-up view of a typical inflorescence of 'Sensation Rose'.

The photograph at the bottom of the second sheet is a close-up view of a typical leaf of 'Sensation Rose'.

DETAILED BOTANICAL DESCRIPTION

The aforementioned photographs, following observations and averaged measurements describe plants grown in Boskoop, The Netherlands, in an outdoor nursery under full sunlight during the spring and early summer with day temperatures ranging from 14° C. to 32° C. and night temperatures ranging from 4° C. to 16° C. Plants were grown in one-gallon containers. Plants had been growing for about two years when the photographs and description were taken. Color references are made to The Royal Horticultural Society Colour Chart, 2001 Edition, except where general terms of ordinary dictionary significance are used.

Botanical classification: *Salvia nemorosa* cultivar 'Sensation Rose'.

Parentage:

*Female, or seed, parent.*—Proprietary selection of *Salvia nemorosa* identified as code number MD1700, not patented.

*Male, or pollen, parent.*—Proprietary selection of *Salvia nemorosa* identified as code number 60608810, not patented.

Propagation:

*Type.*—By cuttings.

*Time to initiate roots, summer.*—About 10 days.

*Time to initiate roots, winter.*—About 14 days.

*Time to produce a rooted young plant, summer.*—About 42 days.

*Time to produce a rooted young plant, winter.*—About 49 days.

*Root description.*—Fine, fibrous.

*Rooting habit.*—Freely branching.

Plant description:

*Form.*—Herbaceous perennial. Mostly upright plant habit to slightly outwardly spreading; broad inverted triangle. Freely branching with about eleven basal stems; low to moderately vigorous growth habit. Flowers arranged in dense verticillasters on spikes.

*Plant height.*—About 27 cm.

*Plant width.*—About 34.5 cm.

*Flowering stem description (peduncles).*—Length (excluding inflorescence): About 15 cm. Diameter: About 4 mm. Internode length: About 2 cm. Strength: Strong. Texture: Densely pubescent. Color: 144A.

*Foliage description.*—Arrangement: Opposite, simple. Length: About 4.1 cm. Width: About 2.1 cm. Shape: Ovate. Apex: Acute. Base: Cordate. Margin: Crenate. Texture, upper and lower surfaces: Sparsely pubescent; rugose. Venation pattern: Pinnate. Color: Developing foliage, upper surface: 137B. Developing foliage, lower surface: 137C. Fully expanded foliage, upper surface: 137A; venation, 138B. Fully expanded foliage, lower surface: Between 137C and 147B; venation, 138B. Petiole: Length: About 8 mm. Diameter: About 3 mm. Texture, upper and lower surfaces: Pubescent. Color, upper and lower surfaces: 138B.

Flower description:

*Flower arrangement and shape.*—Single bilabiate flowers in verticillasters on spikes; flowers face outwardly. Freely flowering, about 78 flowers and flower buds per spike.

*Natural flowering season.*—Continuous from mid-May to early August in The Netherlands.

*Flower longevity on the plant.*—Individual flowers last about one week on the plant. Flowers not persistent.

*Fragrance.*—None detected.

*Flower buds.*—Length: About 7 mm. Diameter: About 4 mm. Shape: Obovate. Color: 67A.

*Inflorescence size.*—Length: About 10.5 cm. Diameter: About 2.6 cm.

*Flowers.*—Diameter: About 9 mm by 5 mm. Depth (height): About 1.4 cm.

*Petals.*—Arrangement: Bilabiate; lips fused at the base. Length: Upper petal: About 1 cm. Lower petal: About 9 mm. Width: Upper petal: About 1.5 mm. Lower petal: About 6 mm. Shape: Upper petal: Broadly elliptic; hooded. Lower petal: Roughly spatulate. Apex: Upper petal: Emarginate. Lower petal: Broadly acute. Margin: Upper petal: Entire. Lower petal: Three-lobed. Texture, upper and lower petals: Sparsely pubescent. Color, when opening and fully opened, upper surface: Upper petal: 75A. Lower petal: Closest to N74C. Color, when opening and fully opened, lower surface: Upper petal: 75A. Lower petal: Closest to N74C.

*Sepals.*—Arrangement: Five sepals fused at base. Length: About 6 mm. Width: About 1 mm. Shape: Elliptic. Apex: Acute. Base: Cuneate. Margin: Entire. Texture, upper and lower surfaces: Smooth. Color: Immature, upper surface: 146B to 146C; longitudinal stripes, 147A. Immature, lower surface: 146A; longitudinal stripes, darker than 147A. Mature, upper surface: 146B to 146C; longitudinal stripes, 147A. Mature, lower surface: 187B tinted with green.

*Peduncles.*—Strength: Strong. Length: About 10.5 mm. Diameter: About 2 mm. Aspect: Erect; secondary peduncles, about 30° from vertical. Texture: Pubescent. Color: 143A to 144A.

*Pedicels.*—Strength: Strong. Length: About 2 mm. Diameter: About 0.5 mm. Aspect: About 35° from vertical. Texture: Pubescent. Color: 182C; towards the base, 144B to 144C.

*Reproductive organs.*—Stamens: Quantity per flower: Two. Filament length: About 7 mm. Filament color: 75D. Anther shape: Linear. Anther length: About 1.5 mm. Anther color: 200B. Pollen amount: Scarce. Pollen color: 200C to 200D. Pistils: Quantity per flower: One. Pistil length: About 1.4 cm. Stigma shape: Two-parted. Stigma color: N74C. Style length: About 1.2 cm. Style color: N74C to N74D. Ovary color: N144D.

*Seed/fruit.*—Seed and fruit production has not been observed.

Disease/pest resistance: Plants of the new *Salvia* have not been noted to be resistant to pathogens and pests common to *Salvia*.

Garden performance: Plants of the new *Salvia* have exhibited good tolerance to rain and wind and have been observed to tolerate temperatures from 0° C. to 30° C.

It is claimed:

1. A new and distinct cultivar of *Salvia* plant named 'Sensation Rose', as illustrated and described.

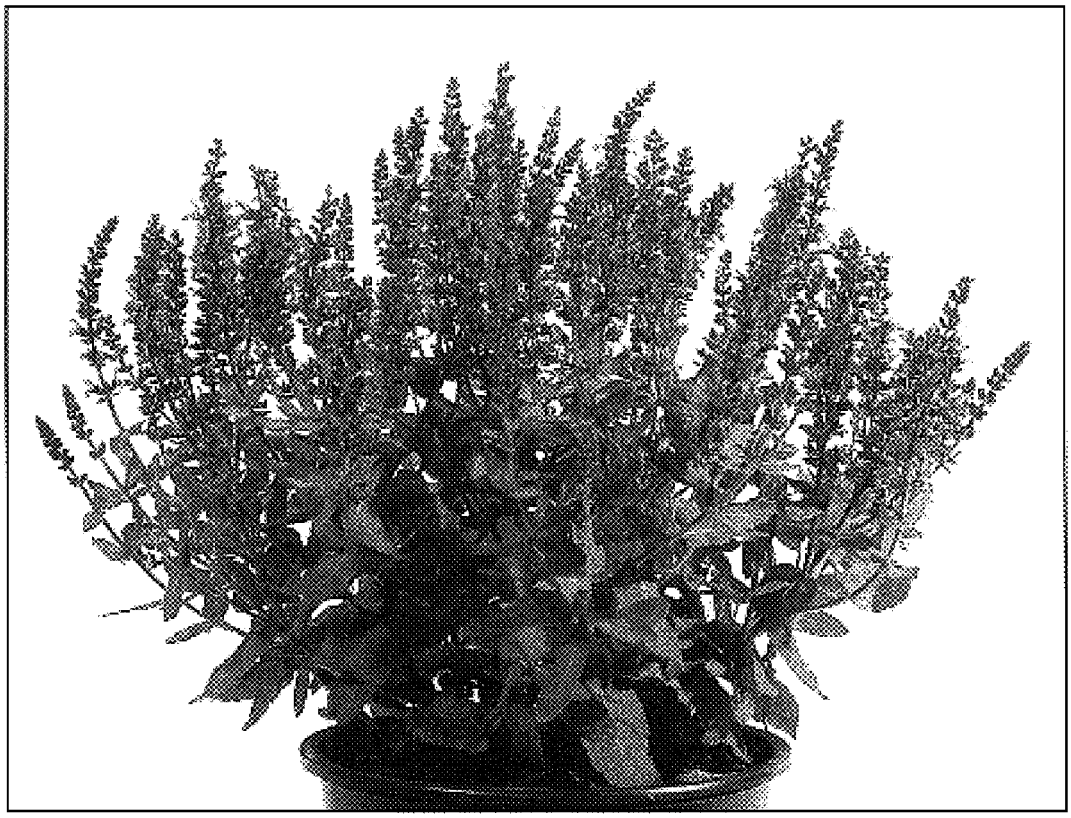

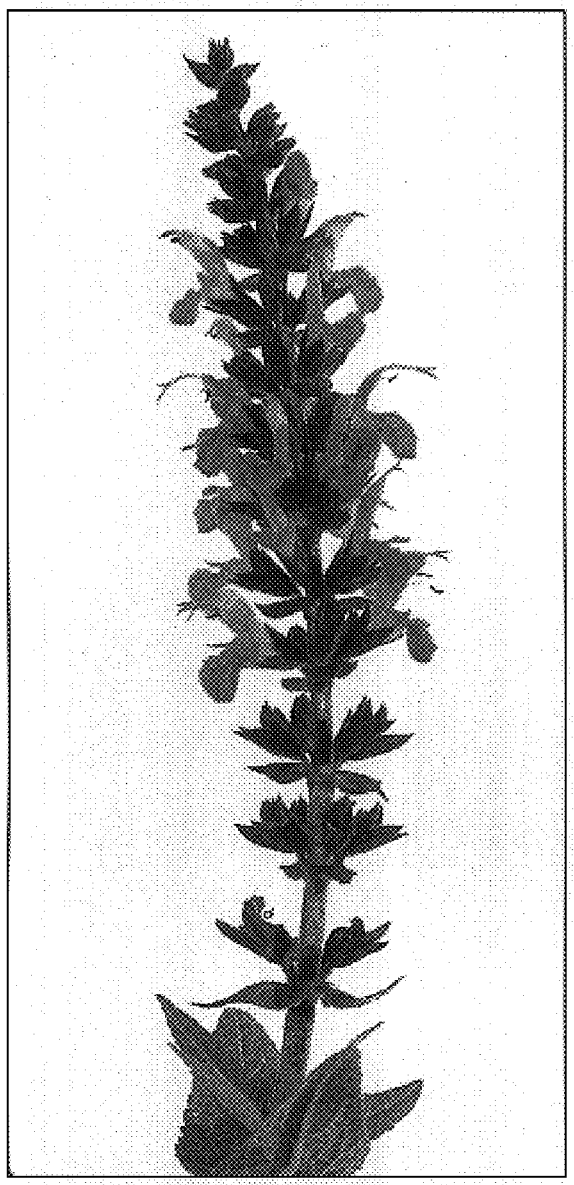
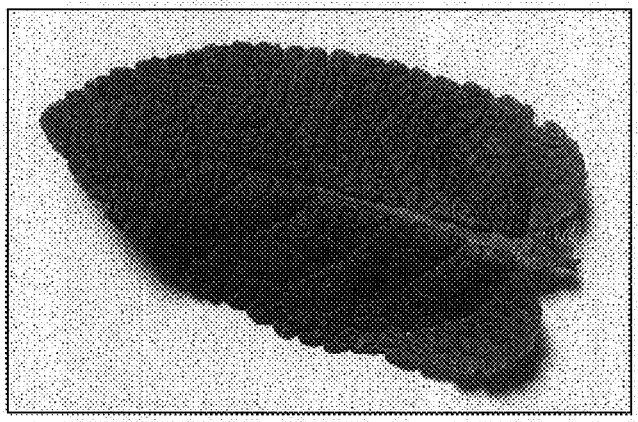

* * * * *